(12) United States Patent
Gemeinhart et al.

(10) Patent No.: US 7,943,569 B2
(45) Date of Patent: May 17, 2011

(54) COMPOSITION AND METHOD FOR PROVIDING LOCALIZED DELIVERY OF A THERAPEUTIC AGENT

(75) Inventors: Richard A. Gemeinhart, Chesterton, IN (US); Jovita R. Tauro, Nanuet, NY (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 595 days.

(21) Appl. No.: 11/941,389

(22) Filed: Nov. 16, 2007

(65) Prior Publication Data

US 2008/0131510 A1 Jun. 5, 2008

Related U.S. Application Data

(63) Continuation-in-part of application No. PCT/US2006/018614, filed on May 15, 2006.

(60) Provisional application No. 60/681,424, filed on May 16, 2005.

(51) Int. Cl.
*A61K 38/00* (2006.01)
*A61K 47/00* (2006.01)

(52) U.S. Cl. ........................................................ 514/1.3

(58) Field of Classification Search ........................... None
See application file for complete search history.

(56) References Cited

U.S. PATENT DOCUMENTS

| | | | |
|---|---|---|---|
| 3,867,329 A * | 2/1975 | Halpern et al. ............ | 210/360.1 |
| 5,514,379 A * | 5/1996 | Weissleder et al. ........... | 424/426 |
| 6,224,903 B1 | 5/2001 | Martin et al. | |
| 6,844,318 B2 | 1/2005 | Copeland et al. | |
| 2002/0103133 A1 | 8/2002 | Copeland et al. | |
| 2003/0195152 A1 | 10/2003 | Suarato et al. | |
| 2004/0001892 A1 | 1/2004 | Healy et al. | |
| 2004/0116348 A1* | 6/2004 | Chau et al. ...................... | 514/12 |
| 2004/0228831 A1 | 11/2004 | Belinka et al. | |

FOREIGN PATENT DOCUMENTS

| WO | WO 0168145 A2 * | 9/2001 |
|---|---|---|
| WO | 02072620 | 9/2002 |
| WO | 2007103364 | 9/2007 |

OTHER PUBLICATIONS

Duncan, Ruth, "The Dawning Era of Polymer Therapeutics", Nature Reviews 2003 2:347-360.
Kost et al., "Responsive polymeric delivery systems", Advanced Drug Delivery Reviews 2001 46:125-148.
Moses et al., "Advancing the field of drug delivery: Taking aim at cancer", Cancer Cell 2003 4:337-341.
Peppas et al., "Poly(ethylene glycol)-containing hydrogels in drug delivery", Journal of Controlled Release 1999 62:81-87.
Turk et al., "Determination of protease cleavage site motifs using mixture-based oriented peptide libraries", Nature Biotechnology 2001 19:661-667.

* cited by examiner

*Primary Examiner* — Robert M Kelly
(74) *Attorney, Agent, or Firm* — Licata & Tyrrell P.C.

(57) ABSTRACT

The present invention is a composition for providing localized delivery of a therapeutic agent to a subject. The instant composition is a hydrophilic matrix-based prodrug system, wherein a protease substrate peptide acts as extracellular protease degradable spacer binding the therapeutic agent to a hydrophilic matrix. Release of the therapeutic agent is achieved by localized activity of extracellular proteases thereby providing minimal toxicity of the therapeutic agent and maximum release with protease activity. Methods for producing the instant composition and providing localized delivery of a therapeutic agent to a subject are also provided.

3 Claims, 4 Drawing Sheets

SEQUENCE LISTING

<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Cys Gly Leu Asp Asp
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Lys Pro Ala Gly Leu Leu Gly Cys
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Gly Pro Ala Gly Leu Leu Gly
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Gly Pro Asn Gly Ile Ala Gly Asn
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Gly Pro Gln Gly Ile Ala Gly Asn
1               5

```
<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Gly Pro Asn Gly Ile Phe Gly Asn
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Gly Pro Leu Gly Val Arg Gly
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Gly Pro Leu Gly Met Phe Ala Thr
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Pro Leu Gly Leu Trp Ala
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Nva

<400> SEQUENCE: 10

Pro Leu Ala Val Gly Ala
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Pro Leu Gly Leu Gly Ala
1               5
```

```
<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Gly Pro Tyr Ala Pro Ala Gly His
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic peptide

<400> SEQUENCE: 13

Gly Pro Asn Gly Ile Leu Gly Asn
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14

Pro Leu Gly Met Leu Ser
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Leu Ile Pro Val Ser Leu Ile Ser
1               5

<210> SEQ ID NO 16
<211> LENGTH: 5
<212> TYPE: PRT
<213> ORGANISM: Artificial sequence
<220> FEATURE:
<223> OTHER INFORMATION: Synthetic peptide

<400> SEQUENCE: 16

Gly Pro Leu Gly Pro
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide

<400> SEQUENCE: 17

Gly Pro Ile Gly Pro
1               5
```

-continued

```
<210> SEQ ID NO 18
<211> LENGTH: 4
<212> TYPE: PRT
<213> ORGANISM: Artificial sequence
<220> FEATURE:
<223> OTHER INFORMATION: Synthetic peptide

<400> SEQUENCE: 18

Ala Pro Gly Leu
1

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Pro Gln Gly Ile Ala Gly Trp
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide

<400> SEQUENCE: 20

Pro Leu Gly Leu Trp Ala
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide

<400> SEQUENCE: 21

Pro Leu Ala Leu Trp Ala Arg
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic peptide

<400> SEQUENCE: 22

Pro Leu Ala Tyr Trp Ala Arg
1               5

<210> SEQ ID NO 23
<211> LENGTH: 8
<212> TYPE: PRT
<213> ORGANISM: Artificial sequence
<220> FEATURE:
<223> OTHER INFORMATION: Synthetic peptide

<400> SEQUENCE: 23

Gly Pro Leu Gly Ile Ala Gly Gln
1               5

<210> SEQ ID NO 24
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 24

Ser Gly Ala Asn Ile Ser Asp Leu Thr Ala
1               5                   10

<210> SEQ ID NO 25
<211> LENGTH: 7
<212> TYPE: PRT
<213> ORGANISM: Artificial sequence
<220> FEATURE:
<223> OTHER INFORMATION: Synthetic peptide

<400> SEQUENCE: 25

Pro Tyr Ala Tyr Trp Met Arg
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic peptide

<400> SEQUENCE: 26

Gly Pro Gln Gly Ile Trp Gly Gln
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic peptide

<400> SEQUENCE: 27

Gly Pro Gln Gly Ile Phe Gly Gln
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic peptide

<400> SEQUENCE: 28

Cys Pro Gly Arg Val Val Gly Gly
1               5

<210> SEQ ID NO 29
<211> LENGTH: 4
<212> TYPE: PRT
<213> ORGANISM: Artificial sequence
<220> FEATURE:
<223> OTHER INFORMATION: Synthetic peptide

<400> SEQUENCE: 29

Cys Pro Gly Arg
1

<210> SEQ ID NO 30
<211> LENGTH: 4
<212> TYPE: PRT
<213> ORGANISM: Artificial sequence
```

```
-continued

<220> FEATURE:
<223> OTHER INFORMATION: Synthetic peptide

<400> SEQUENCE: 30

Gly Asp Lys Pro
1

<210> SEQ ID NO 31
<211> LENGTH: 5
<212> TYPE: PRT
<213> ORGANISM: Artificial sequence
<220> FEATURE:
<223> OTHER INFORMATION: Synthetic peptide

<400> SEQUENCE: 31

Gly Ser Asp Lys Pro
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic peptide

<400> SEQUENCE: 32

Lys Ala Gly Leu Leu Cys
1               5

<210> SEQ ID NO 33
<211> LENGTH: 4
<212> TYPE: PRT
<213> ORGANISM: Artificial sequence
<220> FEATURE:
<223> OTHER INFORMATION: Synthetic peptide

<400> SEQUENCE: 33

Lys Gly Leu Cys
1

<210> SEQ ID NO 34
<211> LENGTH: 4
<212> TYPE: PRT
<213> ORGANISM: Artificial sequence
<220> FEATURE:
<223> OTHER INFORMATION: Synthetic peptide

<400> SEQUENCE: 34

Lys Pro Ala Gly
1
```

COMPOSITION AND METHOD FOR PROVIDING LOCALIZED DELIVERY OF A THERAPEUTIC AGENT

INTRODUCTION

This application is a continuation-in-part application of PCT/US2006/018614, filed May 15, 2006, which claims benefit of U.S. Provisional Patent Application Ser. No. 60/681,424, filed May 16, 2005, the contents of which are incorporated herein by reference in their entireties.

This invention was made in the course of research sponsored by the National Eye Institute (Grant No. R03 EY014357) and National Institutes of Health (Grant No. C06 RR15482). The U.S. government has certain rights in the invention.

BACKGROUND OF THE INVENTION

It has been recognized that the current paradigm of arbitrary and nonspecific delivery of chemotherapeutics can be improved by targeting the activation or release of the chemotherapeutic at a desired site via specific active mechanisms (Moses, et al. (2003) *Cancer Cell* 4:337-341; Kost and Langer (2001) *Adv. Drug Delivery Rev.* 46:125-148). Thus, systems that utilize tumor biology have been proposed and utilized to improve the outcome for brain tumor and other cancer patients (Duncan (2003) *Nat. Rev. Drug Discovery* 2:347-360).

Several aspects of tumor biology have been exploited to utilize tumor biology for delivery of chemotherapeutics, including tissue invasion, angiogenesis, and metastasis. For example, many proteases are implicated in extracellular matrix degradation and matrix metalloproteases have been shown to actively participate in degradation of extracellular matrix and activation of invasion promoting growth factors (Rao, et al. (1996) *Clin. Exp. Metas.* 14:12-18). Matrix metalloproteases play an important and beneficial role in tissue remodeling, wound healing, and angiogenesis along with negative roles in tumor invasion and neovascularization (Woessner (1991) *FASEB J.* 5:2145-2154; Mignatti and Rifkin (1993) *Phys. Rev.* 73:161-185). Unequivocal data confirms that the levels of matrix metalloprotease-2 (MMP-2) and matrix metalloprotease-9 (MMP-9) are observed to increase in correlation with tumor progression in human gliomas (Sawaya, et al. (1996) *Clin. Exp. Metas.* 14:35-42; Forsyth, et al. (1999) *Br. J. Cancer* 79:1828-1835). Initial attempts to exploit matrix metalloproteases as a chemotherapeutic target using synthetic matrix metalloprotease inhibitors prevented glioma invasion by inhibiting matrix metalloprotease activity. Matrix metalloprotease inhibitors reduced glioma growth and invasion in vitro and in animal models (Tonn, et al. (1999) *Int. J. Cancer* 80:764-772; Price, et al. (1999) *Clin. Cancer Res.* 5:845-854) but have achieved disappointing results in Phase I, II, and III clinical trials (Coussens, et al. (2002) *Science* 295:2387-2392). Moreover, prodrug activation by MMPs is disclosed in U.S. patent application Ser. No. 09/808,832 and WO 02/072620. Similarly, attachment of therapeutic agents to soluble polymers via MMP-sensitive linkers is disclosed in U.S. patent application Ser. Nos. 10/437,983 and 10/333,619 and U.S. Pat. No. 6,224,903. Moreover, MMP-sensitive linkers are disclosed for preparing biodegradable hydrogel compositions. See U.S. patent application Ser. Nos. 10/385,900.

SUMMARY OF THE INVENTION

The present invention is an extracellular protease-activated prodrug composed of a hydrophilic matrix having a therapeutic agent linked thereto via an extracellular protease substrate peptide.

The present invention is also a method for producing the extracellular protease-activated prodrug and a method for using the same to provide localized delivery of a therapeutic agent.

BRIEF DESCRIPTION OF THE DRAWINGS

FIG. 3 shows cisplatin release from poly(ethylene glycol) diacrylate (PEGDA) hydrogels.

DETAILED DESCRIPTION OF THE INVENTION

Figure 1:
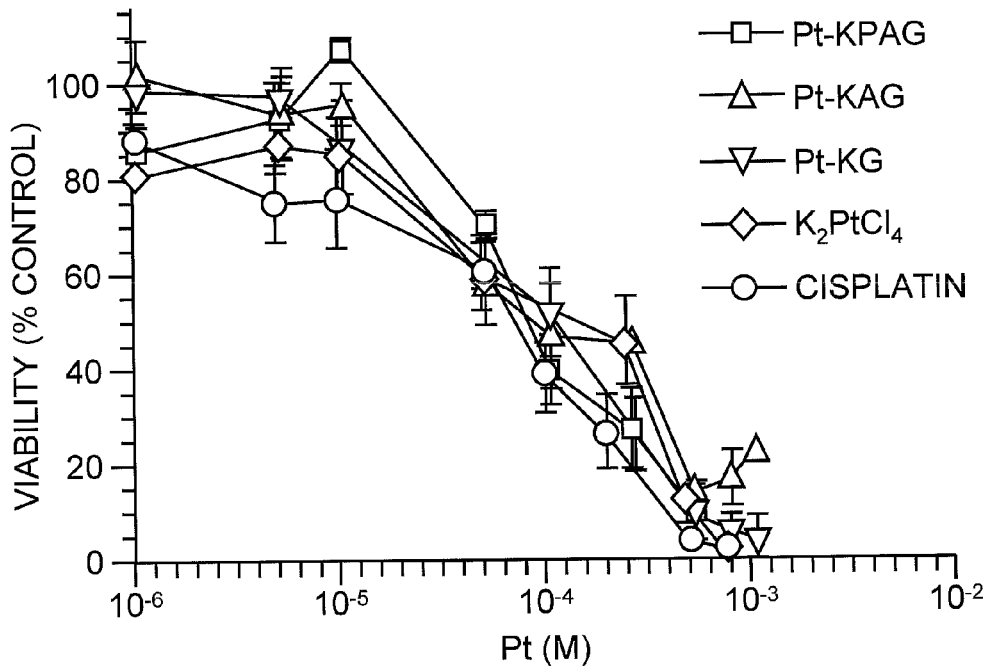
FIG. 1 shows the activity of Pt-peptide complexes as determined by cell viability.

The present invention is an extracellular protease-activated prodrug composed of a hydrophilic matrix having a therapeutic agent linked thereto via an extracellular protease substrate peptide for use in selective, local delivery of the therapeutic agent, wherein higher amounts of therapeutic agents are released in response to disease-associated responses such as metastasis, angiogenesis, and cancer invasion which are associated with elevated levels of extracellular protease. It is contemplated that the instant composition overcomes inadequacies in conventional controlled drug release systems by providing selective delivery to diseased tissue. In the context of cancer prevention and treatment, the instant invention is expected to mitigate cancer recurrence and invasion as therapeutic agent will be activated as a tumor attempts to metastasize or recur locally. Localized delivery minimizes systemic toxicity and targets activation of the therapeutic agent to the site of malignancy.

By way of illustration, the model chemotherapeutic agent cisplatin was incorporated into a poly(ethylene glycol) diacrylate (PEGDA) hydrogel via a peptide-linker composed of a matrix metalloprotease substrate and cisplatin release from the hydrogel was monitored in the presence of matrix metalloproteases. The results of this analysis indicated that the release of cisplatin from a cisplatin-peptide complex incorporated into hydrogels was dependent upon the presence of MMP in the solution, with approximately 35% of platinum released from hydrogels in the presence of MMP and only 10% without MMP. The released drug exhibited the expected anti-proliferative activity over several periods of incubation.

Accordingly, the present invention is a prodrug composition activated by extracellular proteases and use thereof in the localized delivery of a therapeutic agent. As used in the context of the present invention, a prodrug is a compound that undergoes biotransformation via a metabolic process before exhibiting its pharmacological effects. In accordance with the instant invention, a prodrug is said to be activated by virtue of extracellular proteases that release the therapeutic agent from its prodrug form by cleaving the protease substrate peptide linking the therapeutic agent to the hydrophilic matrix.

Many diseases and conditions are associated with an increase in the expression and/or activity of extracellular proteases. For example, overexpression and activation of matrix metalloproteases (MMPs) contributes to collagen breakdown and therefore joint destruction in rheumatoid arthritis and osteoarthritis (Milner and Cawston (2005) *Curr. Drug Targets Inflamm. Allergy* 4(3):363-75). Metalloproteinases also play key roles in angiogenesis and stable and unstable coronary artery disease as they mediate changes in aging and atherosclerosis, the cell membrane, and in myocardial and vascular tissue (Rodriguez-Feo, et al. (2005) *Curr. Pharm. Des.* 11(19):2501-14; Tayebjee, et al. (2005) *Curr. Med. Chem.* 12(8):917-25; Singh, et al. (2004) *Mol. Cell. Biochem.* 263(1-2):241-56). The expression of MMPs have also been implicated in lung, causing destruction of tissue integrity followed by tissue remodeling, which together impair normal pulmonary function leading to diseases including asthma and chronic obstructive pulmonary disease (COPD) (Chakrabarti and Patel (2005) *Exp. Lung Res.* 31(6): 599-621; Demedts, et al. (*Curr. Opin. Pharmacol.* 5(3):257-63; Suzuki, et al. (2004) *Treat Respir. Med.* 3(1):17-27). MMP-2 and MMP-9 are well-known contributors to the proteolytic degradation of extracellular matrix during tumor migration and invasion (Bjorklund and Koivunen (2005) *Biochim. Biophys. Acta.* 1755(1):37-69; Sounni and Noel (2005) *Biochimie* 87(3-4):329-42). Increased presence and activity of MMPs also play a role in periodontitis, peri-implantitis and other oral diseases, such as dental caries and oral cancer (Sorsa, et al. (2004) *Oral Dis.* 10(6):311-8. During endochondral bone formation, a cartilage matrix template, rich in collagen type II, is remodeled by osteoblast-synthesized MMP-13 and replaced by bone, (Bilezikian, et al., Eds., Principles of Bone Biology (Academic Press, Inc., San Diego, Calif., 1996)). Moreover, MMP-13 has been detected in human breast carcinoma tissue (Freije, et al. (1994) *J. Biol. Chem.* 269:16766-16773) and in osteoarthritic cartilage and chondrocytes (Mitchell, et al. (1996) *J. Clin. Invest.* 97:761-768). Although conventionally associated with fibrin clot degradation, tissue plasminogen activator proteins are also extracellular proteases shown to have roles in learning and memory, stress, neuronal degeneration, addiction and Alzheimer's disease (Melchor and Strickland (2005) *Thromb. Haemost.* 93(4):655-60). Moreover, in addition to MMP-2 and MMP-9, plasminogen activators (PA) such as urokinase-type PA (uPA) and tissue-type PA (tPA) have been observed at the invasive margins of brain tumors (Levicar et al. (2003) *Acta Neurochir.* (*Wien*) 145(9):825-38). Extracellular proteases of non-mammalian origin are also known to be associated with disease pathologies. For example, bacterial proteases appear to be involved in activating latent procollagenases or inactivating protease inhibitors of human plasma, and thus contribute to tissue damage and bacterial spread across tissue barriers. (Lahteenmaki, et al. (2001) *FEMS Microbiol. Rev.* 25(5): 531-52).

The instant invention takes advantage of the disease-specific overexpression and/or activation of extracellular proteases to activate prodrugs in a localized manner. As used herein, the terms "localized" or "disease-specific" are used interchangeably to mean delivery of a therapeutic agent within a limited area, i.e., at or near diseased tissue or cells, as opposed to a "systemic" delivery throughout the body of a patient. Systemic therapy often results in a therapeutically ineffective level of a therapeutic agent at the site of interest (tumor, wound, infection and the like). Systemic treatment can also result in serious toxicity. Furthermore, the cost of large amounts of each therapeutic agent used for systemic treatment may restrict therapy. By comparison, localized delivery can reduce systemic side effects by using a fraction of the systemic therapeutic dose to combat the disease or condition.

As indicated above, specific extracellular proteases are associated with specific diseases or conditions. Therefore, the selection of the protease substrate peptide will be dependent upon the disease or condition being treated by the extracellular protease-activated prodrug of the present invention. For example, it is well-known in the art that MMP-2 and MMP-9 are overexpressed or activated in cancer progression, whereas MMP-8 is involved in periodontitis and peri-implantitis. Similarly, MMP-2 and MMP-9 have been reported to be involved in the pathogenesis of airway remodeling in asthma and COPD diseases and MMP-12 in the pathogenesis of COPD. Thus, MMP-2 or MMP-9 substrate peptides are suitable for use in extracellular protease-activated prodrugs for treating cancer, asthma and COPD, whereas MMP-8 protease substrate peptides are suitable for use in extracellular protease-activated prodrugs for treating periodontal diseases or conditions. The selection of the appropriate protease substrate peptide can be readily determined by one of skill in the art in view of proteases known to be associated with particular diseases and/or conditions.

While each MMP has different specificities for the constituents of the extracellular matrix, MMP-2 and MMP-9 show a great amount of overlap in their substrate specificities. Substrates common to both gelatinases include gelatins, collagens IV and V, elastin, and aggrecans (Nagase and Fields (1996) *Biopolymers* 40:399-416). Accordingly, protease substrate peptides recognized by both MMP-2 and MMP-9 can be used to release therapeutic agent at sites were both MMP-2 and MMP-9 are active.

Matrix metalloproteinases and other extracellular matrix proteases cleave primarily at Leu-Gly or Ile-Gly bonds. Illustrative MMP substrate peptides are listed in Table 1.

TABLE 1

| MMP substrate peptide | SEQ ID NO: |
| --- | --- |
| -Gly-Pro-Asn-Gly-Ile-Ala-Gly-Asn- | 4 |
| -Gly-Pro-Gln-Gly-Ile-Ala-Gly-Asn- | 5 |
| -Gly-Pro-Asn-Gly-Ile-Phe-Gly-Asn- | 6 |
| -Gly-Pro-Leu-Gly-Val-Arg-Gly- | 7 |
| -Gly-Pro-Leu-Gly-Met-Phe-Ala-Thr- | 8 |
| -Pro-Leu-Gly-Leu-Trp-Ala- | 9 |
| -Pro-Leu-Ala-Nva-Gly-Ala- | 10 |
| -Pro-Leu-Gly-Leu-Gly-Ala- | 11 |
| -Gly-Pro-Tyr-Ala-Pro-Ala-Gly-His- | 12 |
| -Gly-Pro-Asn-Gly-Ile-Leu-Gly-Asn- | 13 |
| -Pro-Leu-Gly-Met-Leu-Ser- | 14 |
| -Leu-Ile-Pro-Val-Ser-Leu-Ile-Ser- | 15 |
| -Gly-Pro-Leu-Gly-Pro-Z | 16 |
| -Gly-Pro-Ile-Gly-Pro-Z | 17 |
| -Ala-Pro-Gly-Leu-Z | 18 |
| -Pro-Gln-Gly-Ile-Ala-Gly-Trp- | 19 |
| -Pro-Leu-Gly-Leu-Trp-Ala- | 20 |

Illustrative extracellular protease substrate peptides for specific extracellular proteases are listed in Table 2.

TABLE 2

| Extracellular Protease | Protease substrate peptide | SEQ ID NO: |
| --- | --- | --- |
| MMP-1 | -Pro-Leu-Ala-Leu-Trp-Ala-Arg- | 21 |
|  | -Pro-Leu-Ala-Tyr-Trp-Ala-Arg- | 22 |
| MMP-2 | -Cys-Gly-Leu-Asp-Asp- | 1 |
|  | -Gly-Pro-Leu-Gly-Ile-Ala-Gly-Gln- | 23 |
|  | -Ser-Gly-Ala-Asn-Ile-Ser-Asp-Leu-Thr-Ala- | 24 |
|  | -Lys-Pro-Ala-Gly-Leu-Leu-Gly-Cys- | 2 |
| MMP-3 | -Pro-Tyr-Ala-Tyr-Trp-Met-Arg- | 25 |
| MMP-8 | -Gly-Pro-Gln-Gly-Ile-Trp-Gly-Gln- | 26 |
| MMP-9 | -Cys-Gly-Leu-Asp-Asp- | 1 |
|  | -Gly-Pro-Gln-Gly-Ile-Phe-Gly-Gln- | 27 |
|  | -Lys-Pro-Ala-Gly-Leu-Leu-Gly-Cys- | 2 |
| Tissue-Type PA | -Cys-Pro-Gly-Arg-Val-Val-Gly-Gly- | 28 |
| Urokinase-Type PA | -Cys-Pro-Gly-Arg-Val-Val-Gly-Gly- | 28 |
|  | -Glu-Gly-Arg- |  |
|  | -Pro-Gly-Arg- |  |
|  | -Cys-Pro-Gly-Arg- | 29 |
| Angiotensin Converting Enzyme | -Gly-Asp-Lys-Pro- | 30 |
|  | -Gly-Ser-Asp-Lys-Pro- | 31 |
| Plasmin | -Ala-Phe-Lys- |  |

Other suitable protease substrate peptides are known in the art and a comprehensive list of extracellular proteases and their cognate substrate peptides is available at the MEROPS database (see Rawlings, et al. (2002) *Nucl. Acids Res.* 30:343-346).

As used in the context of the instant invention, a protease substrate peptide is an oligopeptide (e.g., 5 to 30 amino acid residues) substrate which is recognized and cleaved by extracellular proteases. In accordance with the instant invention, at least one protease substrate peptide links (e.g., via covalent bonds) a therapeutic agent to a hydrophilic matrix. To increase the effective concentration of a protease substrate peptide in the instant composition, it is contemplated that at least two, three, or more protease substrate peptides are used in tandem to link the therapeutic agent to the hydrophilic matrix.

The protease substrate peptide can be produced by recombinant DNA technology or chemically synthesized, or produced by a combination thereof. Recombinant production is particularly suitable when the therapeutic agent is a protein (e.g., antibody or peptide inhibitor) or enzyme. In this regard, nucleic acids encoding the protein or enzyme of interest and the protease substrate peptide are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. Alternatively, the chimeric nucleic acid molecule can be synthesized by conventional techniques including automated DNA synthesis or polymerase chain reaction (PCR) amplification. PCR amplification of gene fragments can be carried out using anchor primers which give rise to complementary overhangs between two consecutive gene fragments which are subsequently annealed and reamplified to generate a chimeric gene sequence (see, e.g., Current Protocols in Molecular Biology, eds. Ausubel, et al. John Wiley & Sons, 1992). When the protease substrate peptide is a short peptide, nucleic acids encoding the peptide can be incorporated into the 5' or 3' anchor primers used to amplify nucleic acids encoding the therapeutic protein or enzyme (e.g., using add-on PCR). The chimeric protein is then produced by expressing and purifying the chimeric protein using a suitable host such as *E. coli*. Such methods of recombinant protein expression are well-known and routinely practiced by the skilled artisan.

Wherein the protease substrate peptide contains a chemically reactive amino acid, e.g., cysteine or lysine, the protease substrate peptide can be directly conjugated to the hydrophilic matrix therapeutic agent using conventional methodologies. Protease substrate peptides lacking chemically reactive amino acids can be modified so that one or more chemically reactive amino acids (e.g., cys, cys-gly-cys, polyhistidine, or lysine) are added to the C- or N-terminus. Alternatively, a proteinaceous or non-proteinaceous linker can be chemically conjugated to the protease substrate peptide using convention Fmoc or Tboc chemistries. In some embodiments, the hydrophilic matrix is conjugated or linked to the C-terminus of the protease substrate peptide with attachment of the therapeutic agent at the N-terminus. In other embodiments, the hydrophilic matrix is conjugated or linked to the N-terminus of the protease substrate peptide with attachment of the therapeutic agent at the C-terminus. The particular type of conjugation, N-terminal or amine, C-terminal or carboxy, or other linkage will be dependent upon the peptide substrate and therapeutic agent being conjugated.

In accordance with the present invention, a hydrophilic matrix is employed as a solid or semi-solid scaffold or support for delivering a therapeutic agent. In this regard, the therapeutic agent is homogeneously distributed throughout the hydrophilic matrix to form a homogeneous system, also referred to in the art as a matrix system, wherein upon extracellular protease activation by cleavage of the substrate peptide, the therapeutic agent is released from the hydrophilic matrix. This is in contrast to reservoir systems such as nanoparticles wherein the therapeutic agent is encapsulated or entrapped within a polymer shell and released by diffusion or degradation of the polymer.

In particular embodiments, the hydrophilic matrix is a hydrogel. A hydrogel as used herein, refers to a semisolid composition constituting a substantial amount of water. Hydrogels are composed of polymers that will swell without dissolving when placed in water or other biological fluids. Hydrogels can generally absorb a great deal of fluid and, at equilibrium, typically are composed of 60-90% fluid and only 10-30% polymer. Hydrogels are particularly useful due to the inherent biocompatibility of the cross-linked polymeric network (Hill-West, et al. (1994) *Proc. Natl. Acad. Sci. USA* 91:5967-5971). Hydrogel biocompatibility can be attributed to hydrophilicity and ability to imbibe large amounts of biological fluids (Brannon-Peppas. *Preparation and Characterization of Cross-linked Hydrophilic Networks in Absorbent Polymer Technology*, Brannon-Peppas and Harland, Eds. 1990, Elsevier: Amsterdam, pp 45-66; Peppas and Mikos. *Preparation Methods and Structure of Hydrogels in Hydrogels in Medicine and Pharmacy*, Peppas, Ed. 1986, CRC Press: Boca Raton, Fla., pp 1-27). Also, hydrogels closely resemble the natural living extracellular matrix (Ratner and Hoffman. *Synthetic Hydrogels for Biomedical Applications in Hydrogels for Medical and Related Applications*, Andrade, Ed. 1976, American Chemical Society: Washington, D.C., pp 1-36) creating an ideal environment for a matrix to mimic matrix extracellular protease natural activity.

Hydrophilic matrices of the invention can be composed of synthetic hydrophilic polymers which have been synthetically produced and which are hydrophilic, but not necessarily water-soluble. Examples of synthetic hydrophilic polymers which can be used in the practice of the present invention are polyethylene glycol (PEG); polyoxyethylene; polymethylene glycol; polytrimethylene glycols; polyvinylpyrrolidones; poly(acrylic acid); poly(itaconic acid); poly(methacrylic acid); poly(hydroxypropyl acrylamide) (HPMA); poly(peptides) such as polyglutamate, polylysine, polyaspartate, polyserine, polythreonine, polycysteine; and polyoxyethylene-polyoxypropylene block polymers; and copolymers, and derivatives and mixtures thereof. Any hydrophilic polymer capable of being cross-linked (chemically or physically) and conjugated with substrate peptides is embraced by the present invention. While natural marine biopolymers such as agarose, chitosan, and alginate are also embraced by the present invention, in some embodiments, the hydrophilic matrix is not a naturally occurring polymer such as a protein, starch, cellulose, heparin, or hyaluronic acid.

Although different synthetic hydrophilic polymers and selected biopolymers can be used in connection with forming the hydrophilic matrix of the invention, the polymer must be biocompatible and hydrophilic, but crosslinked physically or chemically to prevent dissolution. Particularly suitable polymers include the various forms of derivatized PEG which are extensively used in the modification of biologically active molecules because they lack toxicity, antigenicity, and immunogenicity; have a wide range of solubilities; are generally non-biodegradable and are easily excreted from most living organisms including humans.

Poly(ethylene glycol) diacrylate (PEGDA) hydrogels have been widely accepted in many biomedical applications (Peppas, et al. (1999) *J. Controlled Release* 62:81-87). Hydrogels prepared using, e.g., PEG(574)DA, PEG(4000)DA and PEG(8000)DA, have been demonstrated herein to have adequate physical characteristics for implantation and manipulation prior to placement. PEGDA hydrogels are hydrophilic, biocompatible, nontoxic, and exhibit variable mesh size depending upon PEG macromer length. As exemplified herein, hydrogels containing cisplatin attached via a protease substrate peptide provided a level of control for the release of cisplatin to tumor cells, wherein nonspecific release of the cisplatin was observed for approximately 50% of the bound cisplatin in the first day, regardless of chain length. It is contemplated that increasing therapeutic agent binding efficiency with a hydrophilic matrix such as a PEGDA hydrogel can be achieved by increasing the carboxylic acid content thereby slowing nonspecific release (Yan and Gemeinhart (2005) *J. Controlled Release.* 106:198-208). Alternatively, as exemplified herein, platinum chemistries can be employed when using platinum-based drugs. For example, the platinum group of cisplatin bound to amine groups of the substrate peptide formed a stronger bond than cisplatin bound to carboxy groups. Utilization of covalent coupling of alternate drugs could also alleviate the problem of nonspecific release (Rao, et al. (1996) *Clin. Exp. Metas.* 14:12-18).

Other synthetic polymers with multifunctional sites for conjugating the protease substrate peptide to the hydrophilic matrix as well as cross-linking the hydrophilic matrix also find use in the present invention. Multifunctionally activated synthetic polymers can be prepared using various techniques known in the art which provide functional groups at various locations along the polymer. An example of a multifunctional activated synthetic polymer is monomethoxy-polyethylene glycol (mPEG), which can be activated by the addition of a compound such as cyanuric chloride, then coupled to, e.g., a protein (see Abuchowski, et al. (1977) *J. Biol. Chem.* 252: 3578). Another form of activated PEG is PEG-succinate-N-hydroxysuccinimide ester (SS-PEG) (see Abuchowski, et al. (1984) *Cancer Biochem. Biophys.* 7:175). Activated forms of PEG such as SS-PEG react with proteins under relatively mild conditions and produce conjugates without destroying the specific biological activity and specificity of the protein attached to the PEG. Linkages between PEG and a therapeutic agent are also possible via urethane linkages (see Zalipsky, et al. (1991) Polymeric Drug and Drug Delivery Systems, Chapter 10, *Succinimidyl Carbonates of Polyethylene Glycol*), wherein the stability of urethane linkages has been demonstrated under physiological conditions (Veronese, et al. (1985) *Appl. Biochem. Biotechnol.* 11:141; Larwood, et al. (1984) *J. Labelled Compounds Radiopharm.* 21:603). Another method of attaching a therapeutic agent to PEG is by means of a carbamate linkage (Beauchamp, et al. (1983) *Anal. Biochem.* 131:25; Berger, et al. (1988) *Blood* 71:1641). The carbamate linkage is created by the use of carbonyldiimidazole-activated PEG.

As disclosed herein, large PEG chain lengths allow proteins to diffuse throughout the matrix while smaller PEG chain lengths can be used to control the accessibility of the matrix to specific proteins (Elbert, et al. (2001) *J. Controlled Release* 76:11-25). In this regard, certain embodiments embrace a hydrophilic matrix with a mesh size which allows extracellular proteases to diffuse throughout the matrix.

In addition to functional groups, the polymers of the instant hydrophilic matrix can further contain a means for controlled biodegradation to facilitate removal of the matrix polymer from the subject being treated. For example, PEGDA hydrogels can be made to biodegrade at a faster rate by modification (Sawhney, et al. (1994) *J. Biomed. Mater. Res.* 28:831-838). PEGDA hydrogels can be made biodegradable by incorporating a biodegradable cross linker or by utilizing biodegradable copolymers (Sawhney, et al. (1993) *Macromolecules* 26:581-587; Park, et al. *Biodegradable Hydrogels for Drug Delivery.* 1993, Lancaster, Pa.: Technomic Pub. ix, 252;

Watanabe, et al. (2002) *Biomaterials* 23:4041-4048; Yamini, et al. (1997) *J. Macromol. Sci. A*34:2461-2470). For example, telechelic biodegradable block copolymers, specifically degraded by either plasmin or crude collagenases, have been used in cross-linked hydrogels (West, et al. (1999) *Macromolecules*, 32:241-244). The extent and rate or degradation is controlled by the specific degradation mechanism used thereby limiting accumulation of the hydrophilic matrix at the site of implantation.

In particular embodiments, the instant composition is used in the preparation of a variety of formed implants for use in medical applications. In the instant hydrophilic matrix-based prodrug system, protease substrate peptides act as extracellular protease degradable spacers binding the therapeutic agent to a hydrophilic matrix so that the prodrug is retained at the site of implantation by the hydrophilic matrix. Advantageously, the hydrophilic matrix system is designed to allow release of the therapeutic agent in an extracellular protease dose-dependent manner; when no protease is present, the therapeutic agent is not activated or released, whereas an increase in the concentration of extracellular protease increases the amount of therapeutic agent released from the hydrophilic matrix. This provides minimal toxicity of the therapeutic agent and maximum release with protease activity.

Accordingly, the instant composition is useful for providing localized delivery of a therapeutic agent to a subject. Subjects benefiting from use of the instant composition include subjects disclosed herein with diseases or conditions associated with an increase in the expression and/or activity of extracellular proteases. As such, the composition of the invention is used in the context of the process of proteolytic remodeling of the extracellular matrix, which is essential in tissue morphogenesis during fetal development, inflammation, arthritis, cancer (e.g., breast, ovarian, brain, stomach, lung, colon, prostate, liver, leukemia, lymphoma, carcinoma, sarcoma, or melanoma), wound healing, macular degeneration, retinopathy and tissue regeneration (Massova, et al. (1998) *FASEB J.* 12:1075-1095; Johansson, et al. (1997) *Developmental Dynamics* 208:387-397).

Therapeutic agents which can be linked to the hydrophilic matrix via a protease substrate peptide include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents.

By way of illustration, antimicrobial agents can include antibiotics such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, and the like; and antiparasitic agents, such as pentamidine, and the like.

Anti-inflammatory agents of use in the instant compositions include, e.g., $\alpha$-1-anti-trypsin, $\alpha$-1-antichymotrypsin, and the like; cytokines and interferons, such as $\alpha$-, $\beta$- or $\gamma$-interferon, $\alpha$- or $\beta$-tumor necrosis factor, and the like, and interleukins.

A composition of the invention can include one or more anticancer agents such as cytotoxic or cell proliferation inhibiting agents which act as alkylating agents, enzyme inhibitors, lytic agents, DNA synthesis inhibitors, membrane permeability modifiers, DNA intercalators, mustard derivatives, protein production inhibitors, ribosome inhibitors, apoptosis inducers, angiogenesis inhibitors, neurotoxins, and the like. More specifically the cytotoxic or cell proliferation inhibiting agent delivered by the instant composition can include, for example, 5-fluorouracil (5-FU), taxol and/or taxotere, actinomycin D, adriamycin, azaribine, bleomycin, busulfan, butyric acid, carmustine, chlorambucil, cisplatin, cytarabine, cytarabine, dacarbazine, estrogen, hormone analogs, insulins, hydroxyurea, L-asparaginase, lomustine, melphalan, mercaptopurine, methotrexate, mitomycin C, prednisilone, prednisone, procarbazine, steroids, streptozotocin, testosterone, thioguanine, thiotepa, tributyrin, vinblastine, vincristine, gentamycin, carboplatin, cyclophosphamide, ifosphamide, maphosphamide, retinoic acid, ricin, diphtheria toxoid, venoms, antistatin or other plasminogen derivatives, and functionally equivalent analogs thereof; colony stimulating factors; erythropoietin; steroids; anesthetics; analgesics; and hormones. The above-mentioned drugs can be used to treat, reverse or prevent neoplasias such as glioblastoma multiforme for which convention delivery systems have been inadequate. Neurotoxins, including antibiotics having neurotoxic effects such as gentamycin, can also be used to treat specific disorders, such as Meneir's disease. One or more of the above-mentioned cytotoxins or cell proliferation inhibiting agents can be advantageously combined in the hydrophilic matrix of the invention with any known analgesic, antimicrobial composition, anti-inflammatory compound, antibody, anticoagulant, antiproliferative, cytokine, growth factor, interferon, hormone, hydroxyapatite, lipid, oligonucleotide, osteoinducer, polymer, polysaccharide, proteoglycanproteins (including plasma protein), steroid, vasoconstrictor, vasodilator, vitamin, mineral, stabilizer, and the like.

Other compounds which can be added to the hydrophilic matrix include, but are not limited to, vitamins and other nutritional supplements; hormones; glycoproteins; fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents. Therapeutic agents can be incorporated into the hydrophilic matrix of the invention to delivery therapeutically effective doses of the disclosed agents according to doses well-known in the art.

Depending on the application, the composition of the invention can be used alone or in admixture of a pharmaceutically acceptable carrier in a pharmaceutical composition. Suitable formulations for use in the present invention are found in Remington: The Science and Practice of Pharmacy, Alfonso R. Gennaro, editor, 20th ed. Lippincott Williams & Wilkins: Philadelphia, Pa., 2000. Exemplary carriers include, e.g., water, saline, alcohol, a buffer and the like. The compositions can also contain pharmaceutically acceptable auxiliary substances as required to approximate physiological conditions, such as pH adjusting and buffering agents, tonicity adjusting agents, wetting agents, detergents and the like.

The compositions of the invention can be formulated for any appropriate manner of administration, including for example, topical, intracranial implantation, subcutaneous implantation or intramuscular implantation depending on the site at which the therapeutic agent is to be delivered and the disease or condition be treated.

The invention is described in greater detail by the following non-limiting examples.

Example 1

Materials

The matrix metalloprotease-sensitive protease substrate peptide, Cys-Gly-Leu-Asp-Asp (SEQ ID NO:1), and the expected cleaved fragment, Leu-Asp-Asp (Tauro and Gemeinhart (2004) *Neuro-Oncology* 6:335-336), were synthesized by the University of Illinois at Chicago Research Resources Center with the N-terminal amine blocked by acylation. Remaining MMP substrate peptides were designed based upon the known MMP substrate sequences (Turk, et al. (2001) *Nat. Biotechnol.* 19:661-667). Peptides were purified (approximately 90% pure) by reverse phase high-performance liquid chromatography. Some peptide structures were confirmed by liquid chromatography-mass spectrometry. Select peptides were synthesized with a fluorescein containing lysine (Lys*) for quantitation.

MMP-2 and MMP-9 proenzymes were purchased from CALBIOCHEM (San Diego, Calif.) and activated as suggested by the manufacturer using 4-(hydroxymercury)benzoic acid.

Short-chain PEGDA ($M_n$) 700, PEG(574)DA) macromer was purchased from Sigma-Aldrich Chemical company (Milwaukee, Wis.). Long-chain PEGDA ($M_n$) 4126, PEG(4000)DA) macromer was purchased from Polysciences, Inc. (Warrington, Pa.). PEG(4000) and PEG(8000) was purchased from Fluka Biochemika (Buchs, Switzerland). Acryloyl chloride, triethylamine and molecular sieves were purchased from Aldrich (St. Louis, Mo.) whereas o-phenylenediamine was purchased from Acros Organics (Morris Plains, N.J.). All remaining chemicals were purchased from Fisher Scientific (Fairlawn, N.J.) and used without further purification unless specified.

Example 2

Cancer Model

As a model for cancer, the malignant glioma cell line (U-87MG, ATCC #HTB-14) was grown and maintained in Eagles Minimum Essential Media with 10% fetal bovine serum, 1% penicillin/streptomycin, sodium pyruvate (110 mg/L), L-Glutamine (292 mg/L), and nonessential amino acids at 37° C. in 5% $CO_2$. One day prior to the test, cells were plated at 50,000 cells/mL in supplemented media on 96-well plates. Peptides at different concentrations were incubated with cells for 24 hours. Cell viability, with respect to the untreated control, was determined using a modified MTT assay (CELL TITER 20 96® Aqueous One Solution Cell Proliferation Assay; PROMEGA, Madison, Wis.) (Barltrop, et al. (1991) *Bioorg. Med. Chem. Lett.* 1:661).

Example 3

Peptide Cleavage

Prospective MMP substrate peptides, Lys*-Pro-Ala-Gly-Leu-Leu-Gly-Cys (SEQ ID NO:2), Lys*-Ala-Gly-Leu-Leu-Cys (SEQ ID NO:32), and Lys*-Gly-Leu-Cys (SEQ ID NO:33), were dissolved in a protease buffer containing Tris-HCl (50 mM), NaCl (0.2 M), $CaCl_2.2H_2O$ (10 mM), BRIJ-35 (0.05%) and $ZnSO_4.7H_2O$ (50 μM) (pH=7.4). Activated MMP-2 or MMP-9 was added to the peptide solution at a final concentration of 10 nM. At predetermined time intervals, the reaction was stopped by adding EDTA solution (25 mM). Samples were analyzed using reverse phase high pressure liquid chromatography (HPLC). The HPLC system was composed of a gradient pump connected to a scanning fluorescence detector and a photodiode array detector. Peptides were separated on a ZORBAX Extend-C18 (80 Å, 3.6 μm, 4.6 mm×150 mm) column (Agilent Technologies, Palo Alto, Calif.) using a gradient of 30%-70% of 0.1% trifluoroacetic acid in acetonitrile against 0.1% trifluoroacetic acid in water over a period of 15 minutes at a flow rate of 1 mL/minute. The expected cleaved fragments, Lys*-Pro-Ala-Gly (SEQ ID NO:34), Lys*-Ala-Gly, and Lys*-Gly, were synthesized to confirm HPLC retention times. The HPLC retention time of each fragment was compared to that of the cleaved fragment and the intact peptide using the HPLC conditions described above.

MMP-2 and MMP-9 substrate peptide length was analyzed. As shown in Table 3, a comparison of the specificity ($k_{cat}/K_m$) of the peptides suggested that the hexapeptide was an optimal substrate of the peptides tested. The longest peptide showed higher reaction rate ($k_{cat}$) for both MMP-2 and MMP-9. Although the affinity or binding strength ($K_m$) for the hexapeptide was not the highest, the turnover number ($k_{cat}$) was significantly higher than the other peptides. This resulted in high substrate specificity ($K_m/k_{cat}$) for Lys*-Pro-Ala-Gly-Leu-Leu-Gly-Cys (SEQ ID NO:2). This peptide had better affinity and specificity for MMP-9 than MMP-2, but this peptide would be considered a good substrate for both MMPs. These results indicated that the length of the amino acid sequence around the cleavage site was important for recognition of the substrate by these particular enzymes. Therefore, Lys*-Pro-Ala-Gly-Leu-Leu-Gly-Cys (SEQ ID NO:2) was selected for further analysis of MMP-2 and MMP-9 release of cisplatin in PEGDA hydrogels.

TABLE 3

| | $V_{max}$ (M/s) × $10^{-9}$ | $K_m$ (M) × $10^{-3}$ | $k_{cat}$ ($s^{-1}$) | $K_{cat}/K_m$ ($M^{-1}s^{-1}$) |
|---|---|---|---|---|
| Lys*-Pro-Ala-Gly-Leu-Leu-Gly-Cys (SEQ ID NO: 2) | | | | |
| MMP-2 | 270 ± 120 | 1 ± 0.5 | 10.7 ± 4.8 | 10700 ± 1000 |
| MMP-9 | 240 ± 50 | 0.4 ± 0.1 | 9.6 ± 2.1 | 24000 ± 1000 |
| Lys*-Ala-Gly-Leu-Leu-Cys (SEQ ID NO: 32) | | | | |
| MMP-2 | 6.02 ± 2.1 | 1.4 ± 0.4 | 0.24 ± 0.08 | 170.7 ± 15.2 |
| MMP-9 | 0.99 ± 0.2 | 0.16 ± 0.1 | 0.04 ± 0.01 | 251.6 ± 18.6 |
| Lys*-Gly-Leu-Cys (SEQ ID NO: 33) | | | | |
| MMP-2 | 0.88 ± 0.1 | 0.081 ± 0.02 | 0.035 ± 0.006 | 438.6 ± 20 |
| MMP-9 | 5.3 ± 1 | 0.6 ± 0.1 | 0.21 ± 0.04 | 358.2 ± 10 |

The parent peptide, Gly-Pro-Ala-Gly-Leu-Leu-Gly (SEQ ID NO:3), from which the three peptides were designed is known to be cleaved between glycine and leucine by MMP-2 (Turk, et al. (2001) supra). Comparison of the HPLC chromatogram of the synthesized potential cleaved fragment Lys*-Pro-Ala-Gly (SEQ ID NO:34) with chromatograms of the peptide cleaved by MMP-2 and MMP-9 confirmed that Lys*-Pro-Ala-Gly-Leu-Leu-Gly-Cys (SEQ ID NO:2) was cleaved between glycine and leucine. The cleavage site was not altered by modification or addition of the amino acids on the terminal ends of the peptide.

Intact peptides did not show any toxicity on U-87MG cells after incubation for 24 hours. At concentrations as high as 200 µM, cell viability was equivalent to the untreated control for all peptides. Similarly, all of the cleaved fragments did not show any toxic effects on cells. These results indicated that no toxicity was arising from the peptides themselves. Any observed activity would be due to the complexed platinates once the drugs were attached or included with the peptides.

Example 4

Activity of Peptide-Platinate Complexes

To synthesize Pt-complexes, peptides were dissolved in water and equimolar amounts of potassium tetrachloroplatinate ($K_2PtCl_4$) (Acros Organics, Morris Plains, N.J.) were added to each peptide solution. The solutions were stirred for 20 hours and lyophilized.

Although the difference was not significant, the parent drug, cisplatin ($IC_{50}$ 46.9±15 µM), was more active than $K_2PtCl_4$ ($IC_{50}$=70.7±15 µM). Platinum-complexes showed slightly reduced activity, less than an order of magnitude decrease, compared to cisplatin and $K_2PtCl_4$ (FIG. 1). Not wishing to be bound by theory, it is contemplated that the reduction in activity was caused by some level of steric hindrance to the interaction between Pt and DNA, which is necessary for killing tumor cells. Such reduction in activity is tolerable in order to reduce toxicity to normal cells and have reduced systemic toxicity. Since this system is intended for local delivery, fewer total drug molecules would be required to be administered than when given i.v., given the restricted area of activity. Hence, this reduction in activity is not expected to adversely impact therapeutic efficacy when a local concentration is achieved.

Example 5

Hydrogel Synthesis and Characterization

PEGDA was synthesized using PEG(4000) or PEG(8000) and acryloyl chloride (Hern and Hubbell (1998) *J. Biomed. Mat. Res.* 39(2):266-276). Briefly, PEG (2.5 mmol) was dried in benzene by azeotropic distillation (96° C.). Dried PEG was dissolved in 50 mL methylene chloride and 40 mL was placed in a three neck flask. The solution was flushed with nitrogen for 30 minutes. Triethylamine (15 mmol, 3 moles TEA: 1 PEG hydroxyl end group) and acryloyl chloride (15 mmol, 3 moles acryloyl chloride: 1 PEG hydroxyl end group) was added drop wise. The reaction was stirred overnight at room temperature. The insoluble TEA salts were filtered and PEGDA was precipitated using diethyl ether. The precipitate was filtered and purified by dissolving in methylene chloride and reprecipitated in diethyl ether. This was filtered and dried in vacuum. The product was analyzed by Fourier Transform Infra Red and Raman Spectroscopy (Nexus 870 FT-IR with Raman accessory, Thermo Electron Corporation, Madison, Wis.).

Protease peptide substrate (2 mM) was added to the PEGDA (8 mM-100 mM) in phosphate-buffered saline (pH 7.4) and stirred for 4 hours to overnight. Michael addition of the acrylate group to the sulfhydryl group on cysteine (Heggli, et al. (2003) *Bioconjugate Chem.* 14:967-973) was confirmed using Ellman's reagent (Pierce, Milwaukee, Wis.), thereby quantifying reduction in free sulfhydryl groups (Ellman (1959) *Arch. Biochem. Biophys.* 82:70-77). The solution was then polymerized using ammonium persulfate (APS, 20 mM) and N,N,N,N-tetramethylethylenediamine (TEMED, 51.6 mM) at 37° C. Hydrogels were prepared between two glass slides and cut into 6 mm discs wafers using a biopsy punch.

PEGDA and PEGDA-protease substrate peptide hydrogels reached the critical gelation point within 5 minutes of initiation, but the reaction was continued at 37° C. for a minimum of 1 hour to increase the extent of polymerization. PEG(574) DA hydrogels had a mesh size (21±4 nm) that was smaller than PEG(4000)DA hydrogels (79±7 nm) and PEG(8000)DA hydrogels (131±4 nm). Because PEG(4000)DA and PEG(8000)DA hydrogels have significantly longer PEG chains; this increased mesh size allows for substantially higher water content. This larger mesh size was expected to allow MMP-2 and MMP-9 to more freely diffuse in the PEG(4000)DA hydrogel and PEG(8000)DA hydrogel than the PEG(574)DA hydrogel.

The PEG(4000)DA hydrogels with the substrate peptide showed slightly but not significantly higher weight (2.38±0.09. vs. 2.09±0.05) and volumetric swelling (10.8±2.6 vs. 8.6±0.7) ratios than without the peptide. PEG(8000)DA hydrogels with the peptide showed higher weight (2.6±0.02 vs. 2.15±0.02) but lower volumetric swelling (8.9±0.09 vs. 10.7±2.0) ratios than without the peptide. There was no difference in the molecular weights between cross-links, which is expected as the pendant peptides do not play a role in cross-linking; i.e. the mesh size for PEG(8000)DA was 12.6±0.7 nm and 13.1±0.4 nm for hydrogels with and without peptide, respectively.

Protease substrate peptide-PEGDA conjugation was nearly complete after overnight incubation at room temperature as determined by quantitative analysis of free sulfhydryl groups. There was 74.1±3.2% efficiency for conjugation with the PEG(574)DA and 76.1±1% efficiency for conjugation with the PEG(4000)DA, and the reaction did not proceed further following extended incubation under these conditions. Since this reaction mixture was not further purified prior to polymerization; additional incorporation of the protease substrate peptide could be expected by further Michael reaction or chain-transfer reactions with the peptide (Fussell and Cooper (2004) *J. Biomed. Mater. Res. Part A.* 70A:265-273). In similar studies with fluorescent-labeled protease substrate peptide, no peptide was released from the hydrogel without addition of matrix metalloproteases.

To load Pt, the hydrogels were washed repeatedly in double deionized water and dried in vacuo. The dried hydrogels were immersed in a solution of $K_2PtCl_4$ (0.2 mg/mL) and allowed to swell for 20 hours. The hydrogels were then repeatedly washed in phosphate-buffered saline to remove excess Pt. Platinum and peptide incorporated into the hydrogels was determined by mass balance. Hydrogels with and without the peptide were characterized with respect to swelling ratio, molecular weight between cross-links and mesh size (Canal & Peppas (1989) *J. Biomed. Mater. Res.* 23:1183-1193).

The amount of Pt found to be retained as a complex with the peptide in the PEG(8000)DA hydrogel was found to be 16.4±1.2 µg per disc (0.065 µg/mm$^3$, 0.3 nmoles/mm$^3$). This amount (84 nMoles) is higher than the theoretical amount of peptide (43 nMoles) in each disc. This may be due to some adsorption of Pt within the hydrogel or attachment of excess Pt to secondary amine groups, i.e., two moles of Pt complex with one peptide (Anandhi, et al. (2003) *Inorg. Chem.* 42:1282-1295). After repeated washings, the amount of peptide incorporated within the PEG(8000)DA hydrogel was found to be 65.2±1.3% of the original amount added before polymerization due to an aggressive loading protocol that was utilized to attempt to load a maximum amount of platinum possible.

Example 6

Complexation with Carboxyl Groups

Cisplatin was also complexed with the carboxyl groups of substrate peptides. Carboxy-conjugation of cisplatin with aspartic acids in the substrate peptide is depicted in Scheme 1 (Gianasi, et al. (2002) *J. Drug Target* 10:549-556).

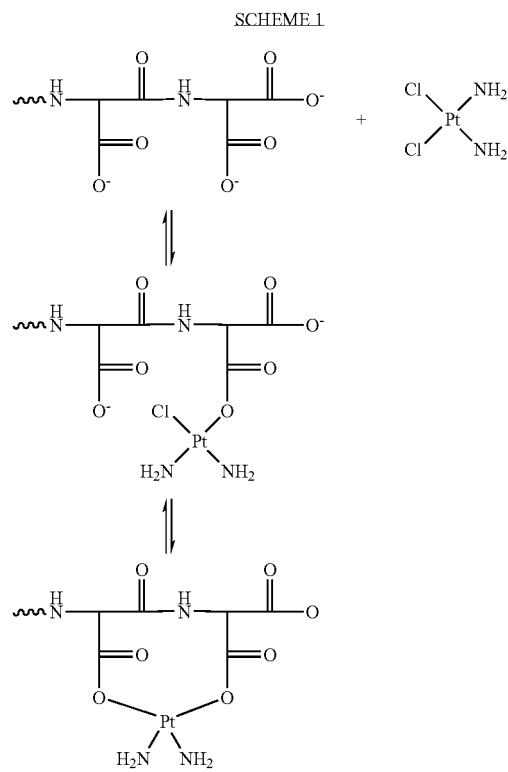

For carboxy-conjugated cisplatin to Cys-Gly-Leu-Asp-Asp (SEQ ID NO:1), cisplatin was aquated at pH 7.4 using silver nitrate (Gianasi, et al. (2002) *J. Drug Target* 10:549-556) and reacted overnight with hydrogels. Hydrogels containing the protease substrate peptide were washed to remove excess cisplatin. Cisplatin was entrapped in hydrogels without protease substrate peptide by using the same procedure as described without washing. Cisplatin entrapment and complexation in hydrogels was determined by spectrophotometeric o-phenylenediamine (OPDA) assay (Golla and Ayres (1973) *Talanta* 20:199-210). The mesh size (ξ) of hydrogels was determined to compare with matrix metalloprotease penetration (Peppas. Characterization of the *Cross-Linked Structure of Hydrogels*. In *Hydrogels in Medicine and Pharmacy*, Peppas, Ed. 1987, CRC Press, Inc.: Boca Raton, Fla., pp 27-56). Entrapped cisplatin content was found to be much higher than complexed cisplatin content since washing removed cisplatin that was not complexed to the hydrogel. PEG(574)DA entrapped 22.1±0.9 µg (0.317 µg/mm$^3$), and 8.6±0.1 µg (0.122 µg/mm$^3$) was retained as cisplatin-hydrogel complexes. Also, the cisplatin content was found to be higher in the PEG(4000)DA hydrogels than in the PEG(574) DA hydrogels. PEG(4000)DA hydrogels entrapped 55.7±6.1 µg (0.43 µg/mm$^3$), while 20.5±1.4 µg (0.157 µg/mm$^3$) was retained as protease substrate peptide-cisplatin complexes.

Example 7

Platinum Release

Hydrogels containing substrate peptide and Pt were placed in 0.5 mL of buffer (pH 7.4) containing Tris-HCl (50 mM), NaCl (0.2 M), CaCl$_2$.2H$_2$O (10 mM), BRIJ-35 (0.05%) and ZnSO$_4$.7H$_2$O (50 µM). Activated MMP-2 or MMP-9 was added to individual wells at a final concentration of 10 nM. MMPs were not added to control wells. Samples were taken at predetermined time intervals and fluorescence intensity, platinum amount (oPDA), and identity (HPLC) in the release media was determined. Wells were spiked at 32 hours with respective MMPs to maintain constant enzymatic activity. Release was compared to Pt release for hydrogels with entrapped Pt; no peptide was present in the hydrogel for entrapped Pt studies which act as a diffusional release control.

Figure 2:
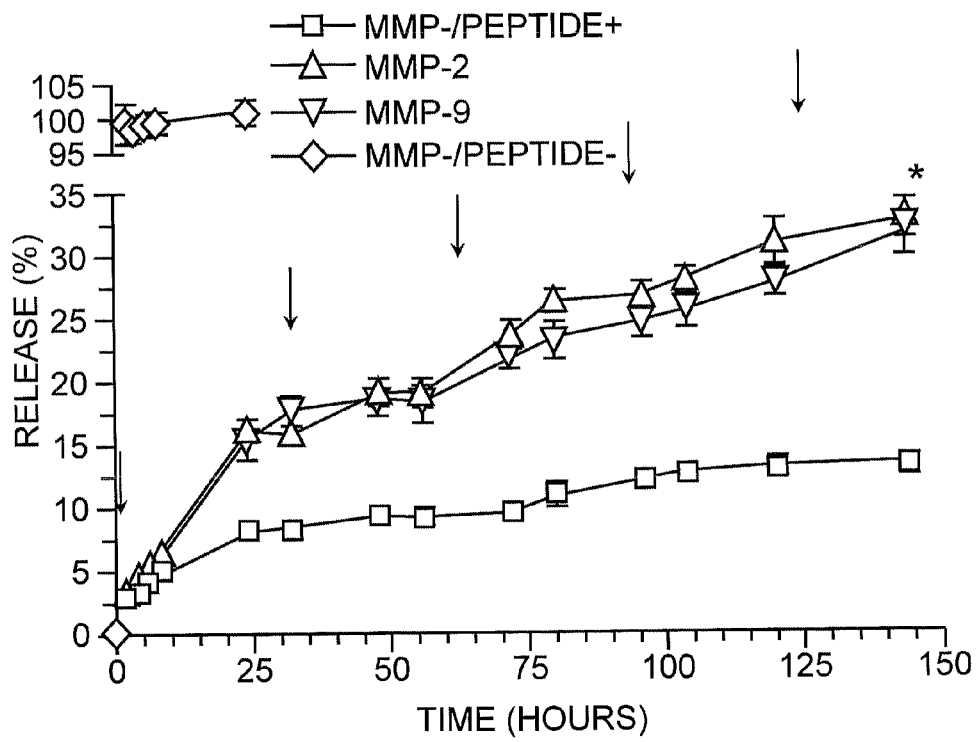
FIG. 2 shows the release of the cleaved peptide fragment from PEG(8000)DA hydrogels in the presence of MMP-2 (10 nM) and MMP-9 (10 nM) compared to non-specific release in the absence of MMPs. Also shown is Pt release when no peptide is present. Arrows indicate addition of MMP to maintain constant activity, and * indicates significant difference from non-specific release (p<0.05, n=3).

The results of this analysis indicated that the addition of MMP-2 and MMP-9 showed a significantly higher release of cleaved fragment from the PEG(8000)DA hydrogels compared to the control (FIG. 2). The release did not plateau before 144 hours as long as additional MMP was added. There was an increased response to the addition of MMPs every 32 hours. The increased response indicated that a constant release of Pt could be obtained with constant availability of active MMPs. Analysis of the supernatant from 6 days with reverse phase HPLC 20 confirmed that the cleaved fragment Pt-Lys*-Pro-Ala-Gly (SEQ ID NO:34) was released. This data further indicated that MMPs were able to show activity on the peptides incorporated in the hydrogel. Non-specific release of Pt from amino groups of the peptide was very low indicating a strong peptide-Pt complex. In contrast to the complexed Pt, all entrapped Pt was instantaneously released within 24 hours.

In addition to PEG(8000)DA hydrogels, there was significant release of cleaved fragment cisplatin-Lys*-Pro-Ala-Gly (SEQ ID NO:32) from PEG(4000)DA hydrogels with addition of MMP-2 and MMP-9. In the absence of MMPs the release was much lower and the difference in the specific and non-specific release showed a plateau after 24 hours. The amount of Pt detected correlated with the amount of non-specific peptide release. Thus, Pt release appeared to be due to non-specific peptide release from the hydrogel rather than the dissociation of the complex.

Hydrogels with entrapped cisplatin showed an instantaneous burst release; almost 100% of entrapped cisplatin was released within 24 hours. In contrast, cisplatin in complex with the hydrogel exhibited a constant release of cisplatin in the presence of MMPs. Moreover, PEG(8000)DA hydrogels were more responsive to presence and addition of MMPs than PEG(4000)DA, likely due to the increase in diffusion of the MMPs through the higher mesh size.

Figure 3A:
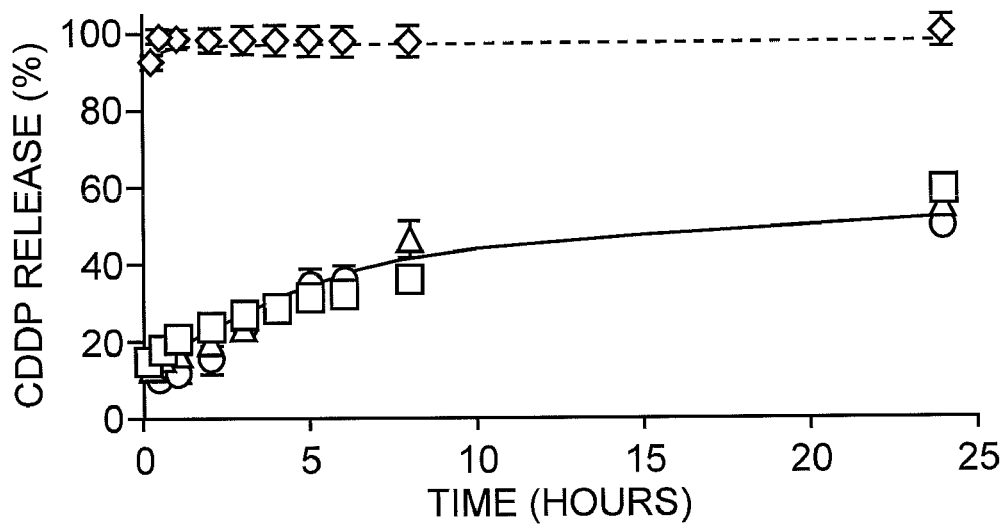
FIG. 3A, cisplatin release from PEG(574)DA hydrogels where cisplatin was entrapped with no complexation (diamond), cisplatin was complexed to the hydrogel (square), cisplatin was complexed to the hydrogel with MMP-9 added to the release media (10 nM) (circle), and cisplatin was complexed to the hydrogel with MMP-2 added to the release media (10 nM) (triangle).
Figure 3B:
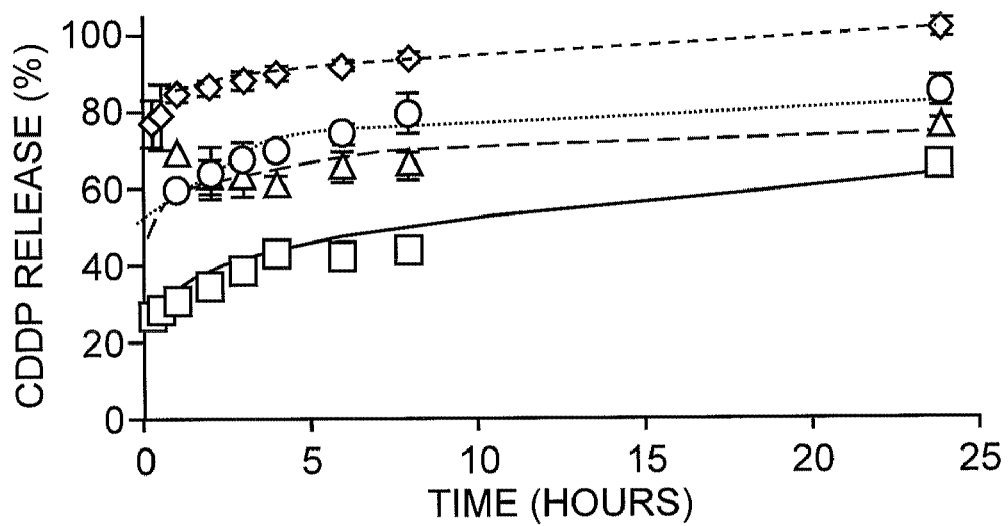
FIG. 3B, cisplatin release from PEG(4000)DA hydrogels where cisplatin was entrapped with no complexation (diamond), cisplatin was complexed to the hydrogel (square), cisplatin was complexed to the hydrogel with MMP-9 added to the release media (10 nM) (circle), and cisplatin was complexed to the hydrogel with MMP-2 added to the release media (10 nM) (triangle).

Cisplatin was nearly instantaneously released in a burst profile (FIGS. 3A and 3B) in PEG(574)DA and PEG(4000) DA hydrogels entrapped with no carboxylic content. Cisplatin complexed with a matrix metalloprotease substrate peptide exhibited slow release over time, even without matrix metalloproteases present, indicating that complexation took place but was not sufficient for complete retention of the drug. However, with the addition of matrix metalloproteases, there was a marked increase in the amount of cisplatin released from the PEG(4000)DA hydrogels (FIG. 3A) but not the PEG(574)DA hydrogels (FIG. 3B). This indicates that the PEG(4000)DA hydrogel allowed sufficient diffusion of the matrix metalloproteases throughout the matrix to cleave the matrix metalloprotease substrate peptide Cys-Gly-Leu-Asp-Asp (SEQ ID NO:1).

Example 8

Cell Culture and MMP Activity

Hydrogels (PEG), hydrogels with peptide (PEG-P), and hydrogels with peptide complexed Pt (PEG-P-Pt) were incubated with U-87 MG cells in supplemented serum-free media for 48 hours. Matrix metalloprotease (10 nM) or control (no MMP) was added to media for specific wells to supplement the MMPs expressed by U-87MG cells. Matrix metalloprotease (10 nM) without hydrogels was examined as a control. Additional MMPs were added at 32 hours to maintain nearly constant MMP activity. Cell viability with respect to the respective controls was calculated using a modified MTS assay.

To determine activity of Pt released longer than 48 hours, hydrogels were placed in serum-free media in the presence and absence of MMP-2 or MMP-9. Activated MMPs were added every 32 hours as in the previous studies. All conditions were maintained similar to the release studies. At 48 and 96 hours, the supernatant media was added to adherent U-87 MG cells in a 96-well plate. After 24 hours of treatment, cell viability with respect to the respective controls was calculated using the modified MTS assay.

To confirm matrix metalloprotease expression and activity in U-87 MG cells, the serum-free media was removed and analyzed for presence for matrix metalloproteases by gelatin zymography (Munaut, et al. (2003) *Int. J. Cancer* 106:848-855). Cell-treated media (10 µL) was loaded on READY GEL zymography gels (BIO-RAD Laboratories, Hercules, Calif.) and electrophoresed at 100 V. The gels were then washed, incubated, stained, and analyzed for presence of matrix metalloproteases.

U-87 MG cells expressed MMP-2 when cultured in media for 24 and 48 hours. Pro-MMP-2 increased as cells were incubated for extended periods. Active MMP-2 was detected at 48 hours. MMP-9 was not expressed at detectable levels in the cells for up to 48 hours. However, this cell line is used as an in vitro model since the expression and functions of MMP-2 and MMP-9 are known to be heterogeneous in clinical GBM presentation (Rao, et al. (1996) *Clin. Exp. Metas.* 14:12-18; Sawaya, et al. (1996) *Clin. Exp. Metas.* 14:35-42) and MMP-2 and MMP-9 have overlapping substrate specificities.

Figure 4:
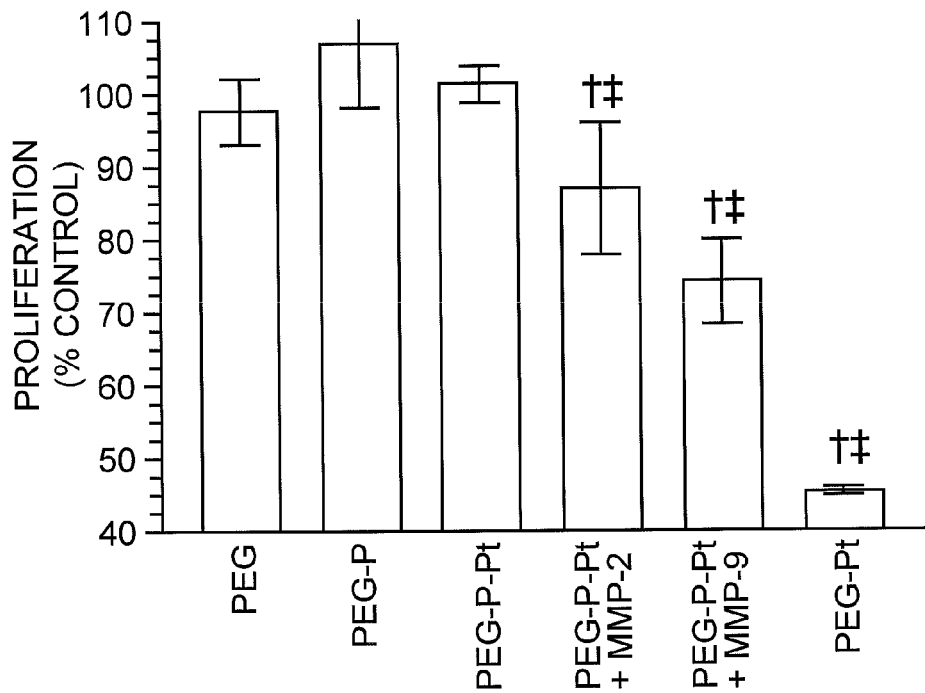
FIG. 4 shows the activity of PEG(8000)DA hydrogels toward U-87 MG cells. Hydrogels without Pt or peptide (PEG), hydrogels with peptide incorporated but without Pt (PEGP), hydrogels with peptide-Pt complex in the absence (PEG-P-Pt) and presence of MMP-2 (PEG-P-Pt+MMP2) or MMP-9 (PEG-P-Pt+MMP9), and hydrogels with entrapped Pt without peptide for complexation (PEG-Pt) were analyzed. † indicates significant difference from negative control (PEG) and ‡ indicates significant difference from positive control (PEGP-Pt) (P<0.05, n=3).

PEG(8000)DA hydrogels without Pt (PEG-P) did not show any activity toward cells. Entrapped Pt (PEG-Pt) showed the greatest activity due to instantaneous release of Pt. Since the amount of Pt loaded within the hydrogel was nearly equivalent to that loaded in the other hydrogels, the activity of the released Pt was only approximately 45% and not completely inhibited. When MMP selective hydrogels were incubated with the cells for 48 hours, hydrogels with complexed Pt (PEG-P-Pt) showed significantly higher activity only in the presence of MMP-2 and MMP-9 compared to those without peptide and Pt (PEG) (FIG. 4). There was also significantly higher activity with addition of MMPs than in the absence of MMPs with hydrogels containing peptide and Pt (PEG-PPt).

Figure 5:
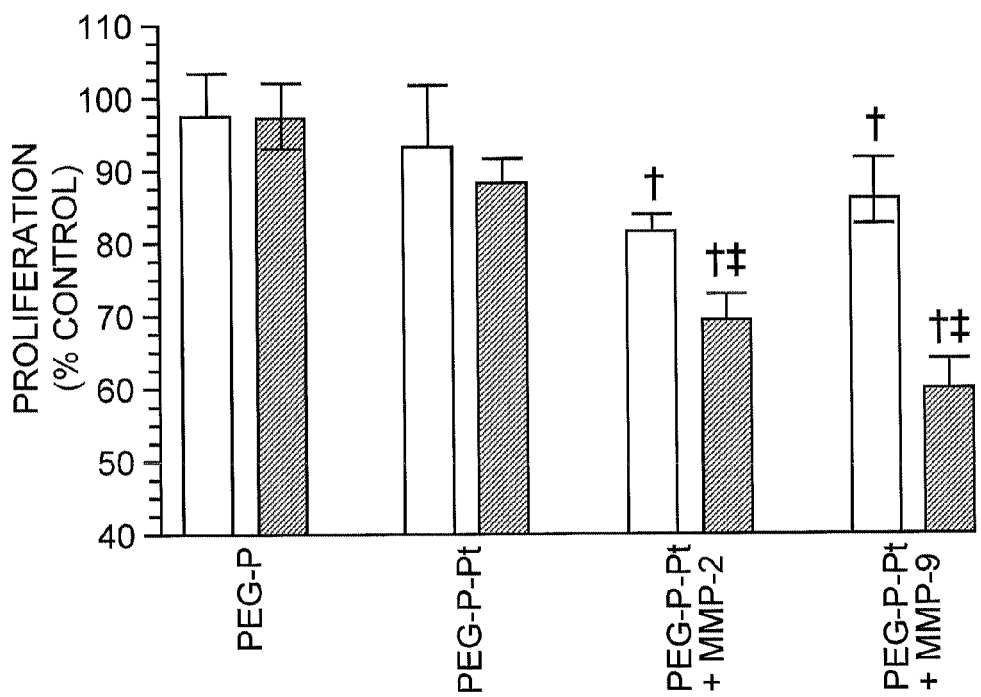
FIG. 5 shows the activity of Pt released from PEG(8000) DA hydrogels into media after 48 hours (open bars) and 96 hours (filled bars) on U-87 MG cells. Hydrogels with peptide incorporated but without Pt (PEG-P), hydrogels with peptide-Pt complex in the absence (PEG-P-Pt) and presence of MMP-2 (PEG-P-Pt+MMP2) or MMP-9 (PEG-P-Pt+MMP9) were analyzed. † indicates significant difference from PEG and ‡ indicates significant difference from PEG-P-Pt (P<0.05, n=3).

When hydrogels were incubated for longer periods with MMPs and the released drug then incubated with cells, a similar trend was observed (FIG. 5). There was significantly higher activity seen with longer incubation times (96 hours) and in the presence of MMPs. The actual activity (viability of 76% with MMP-2 and 69% with MMP-9) was slightly lower, but within close range of the theoretical activity calculated from the release and activity studies (approximately 66% viability), when hydrogels were incubated with cells. Cells in the presence of PEG-P-Pt hydrogels with added MMPs exhibited morphology typical of dying cells while cells in contact with hydrogels without Pt and PEG-P-Pt hydrogels in the absence of MMPs show normal morphology.

Figure 6:
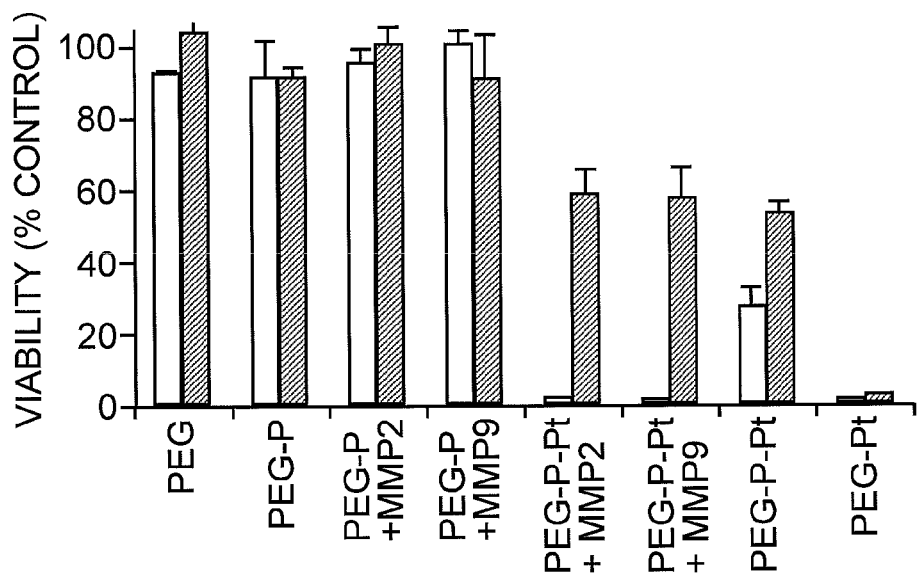
FIG. 6 shows the activity of cisplatin released from PEG-(574)DA (filled bars) and PEG(4000)DA (open bars) hydrogels. Hydrogels without cisplatin or peptides (PEG), hydrogels with peptide incorporated but with cisplatin in the absence (PEG-P), and presence of MMP-2 (PEG-P+MMP2) or MMP-9 (PEG-P+MMP9), hydrogels with entrapped cisplatin but without peptide for complexation (PEG-Pt), and hydrogels with peptide-cisplatin complex in the absence (PEG-P-Pt) and presence of MMP-2 (PEG-P-Pt+MMP2) or MMP-9 (PEG-P-Pt+MMP9).

Moreover, PEG-(574)DA and PEG(4000)DA hydrogels and PEGDA-protease substrate peptide hydrogels without cisplatin were not cytotoxic in the presence or absence of MMP-2 or MMP-9 (FIG. 6). Cisplatin entrapped in PEGDA hydrogels exhibited similar activity to the amount of cisplatin that was loaded into the hydrogel. Upon complexation, PEGDA-protease substrate peptide-cisplatin hydrogels exhibited activity at a level below the amount of cisplatin loaded. Activity of cisplatin released from PEG(574)DA-substrate peptide-cisplatin complex hydrogels was not influenced by matrix metalloprotease addition. Cisplatin released from PEG(4000)DA-substrate peptide-cisplatin complex hydrogels showed higher activity than cisplatin released from PEG(574)DA hydrogels with and without the addition of matrix metalloproteases. Also, with the addition of MMP-2 or MMP-9 to PEG(4000)DA-substrate peptide-cisplatin complex hydrogels, higher cisplatin activity was observed than in the absence of matrix metalloproteases. This was not seen with the PEG(574)DA hydrogels. The increase in cisplatin activity further indicates that more cisplatin was released in the presence of matrix metalloproteases and extracellular proteases can be used to activate prodrugs linked to hydrophilic matrices.

Example 9

Statistical Analysis

Experiments were performed in triplicate at a minimum (n=3). Analysis of Variance (ANOVA) was used to determine significant difference between groups. Bonferroni's test was used for post hoc analysis with a p-value less than 0.05 being statistically significant.

Example 10

Matrigel™ Invasion Assay

Invasion of glioma cells in vitro was measured by the invasion of cells through Matrigel™-coated transwell inserts. The inserts contained an 8 µm pore size polycarbonate membrane over which a thin layer of Matrigel™ was dried. An ECM layer occluded the membrane pores, blocking non-invasive cells from passing through. Matrigel™ chambers were rehydrated with serum-free EMEM for 2 hours at 37° C. in 5% $CO_2$. Then, medium was carefully removed from the inserts without disturbing the membrane. EMEM with 10% fetal bovine serum (750 µL) was added to lower wells as chemoattractant. Cells were trypsinized and 500 µL of cell suspension ($1 \times 10^5$ cells/mL) per condition were added in duplicate or triplicate to the inserts transferred to the wells. Cisplatin, at $LC_{50}$ treatment, was prepared by adding cisplatin solution in serum-free EMEM to the cell suspension to give final cisplatin concentration of 40 µM. For treatments with PEGDA-peptide-cisplatin and cisplatin-PEGDA gels, gels were transferred to the inserts immediately following addition of cell suspensions. After 22 hours, cells that had passed through the filter on the bottom side of the membrane were fixed in 100% methanol and stained using 1% Toluidine blue solution in 1% borax for 4 minutes. Number of invaded cells were than counted under a light microscope at 40× magnification.

Figure 7:
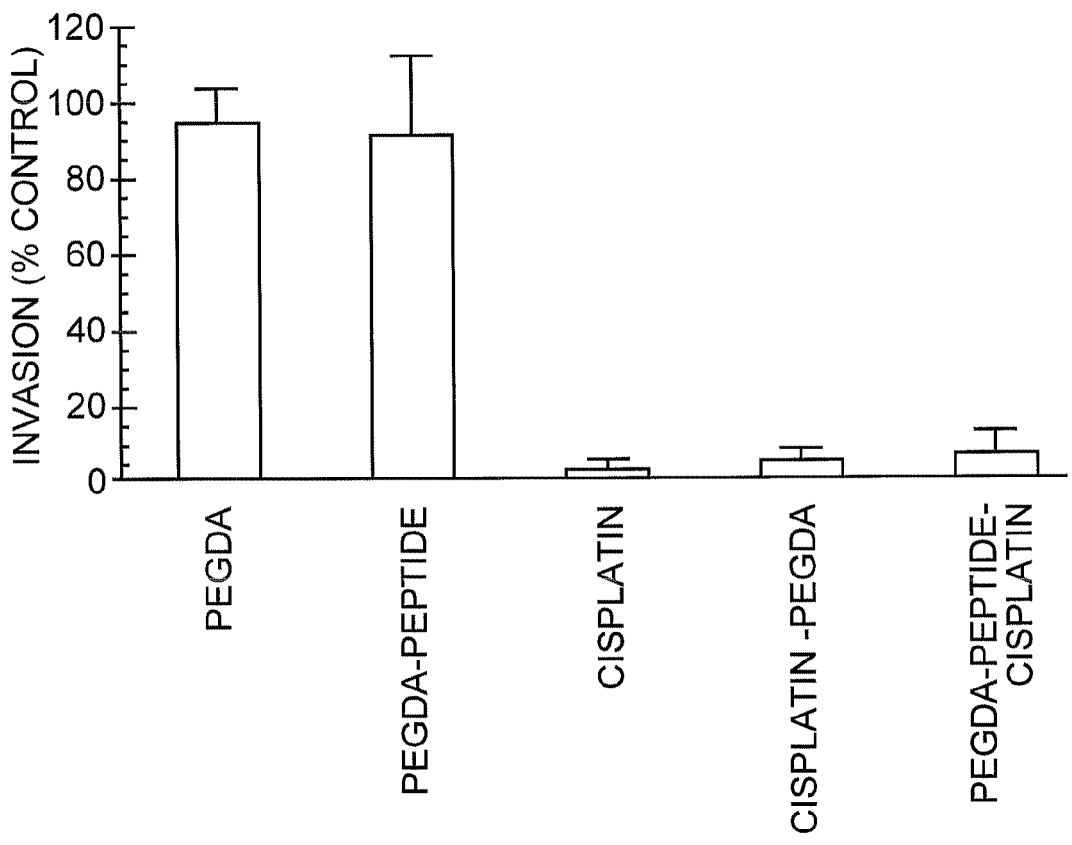
FIG. 7 shows the invasion inhibitory effect of hydrogel (PEGDA), cisplatin, hydrogel with peptide (PEGDA-peptide), cisplatin entrapped in a hydrogel (cisplatin-PEGDA), and the test hydrogel system with cisplatin complexed to MMP-sensitive peptides pendant within a hydrogel (PEGDA-peptide-cisplatin).

If invasion in the absence of any treatment is considered to be 100%, invasion observed when the cells were exposed to cisplatin-PEGDA and PEGDA-peptide-cisplatin hydrogels was significantly lower than that obtained with control PEGDA and PEGDA-peptide hydrogels (FIG. 7). Lower invasion observed with PEGDA-peptide-cisplatin hydrogel indicated activation of cisplatin from the hdyrogel delivery system by MMP-2 and MMP-9 expressed by invasive U87MG cells. Cisplatin was released from the hydrogels by MMP-activation thereby locally preventing invasion of glioma cells.

---

What is claimed is:

1. An extracellular protease-activated prodrug comprising a hydrophilic matrix having a therapeutic agent linked thereto via an extracellular protease substrate peptide of SEQ ID NO:2.

2. A method for producing an extracellular protease-activated prodrug comprising linking a therapeutic agent to a hydrophilic matrix via an extracellular protease substrate peptide of SEQ ID NO:2 thereby producing an extracellular protease-activated prodrug.

3. A method for providing localized delivery of a therapeutic agent comprising administering an extracellular protease-activated prodrug of claim 1, wherein in the presence of an extracellular protease said prodrug is activated thereby providing localized delivery of the therapeutic agent.

* * * * *